(12) United States Patent
Hagen et al.

(10) Patent No.: US 11,460,430 B2
(45) Date of Patent: Oct. 4, 2022

(54) SWEAT SIMULATION, COLLECTING AND SENSING SYSTEMS

(71) Applicant: University of Cincinnati, Cincinnati, OH (US)

(72) Inventors: Joshua A. Hagen, Cincinnati, OH (US); Jason Charles Heikenfeld, Cincinnati, OH (US); Ian Papautsky, Willowbrook, IL (US); Linlin Hou, Portland, OH (US); Rajesh Naik, Centerville, OH (US); Nancy Kelley-Loughnane, Cincinnati, OH (US); Morley O. Stone, Columbus, OH (US); John Busbee, Washington Township, OH (US); Xiao Wang, Waltham, MA (US)

(73) Assignee: University Of Cincinnati, Cincinnati, OH (US)

( * ) Notice: Subject to any disclaimer, the term of this patent is extended or adjusted under 35 U.S.C. 154(b) by 936 days.

(21) Appl. No.: 14/388,416

(22) PCT Filed: Apr. 3, 2013

(86) PCT No.: PCT/US2013/035092
§ 371 (c)(1),
(2) Date: Sep. 26, 2014

(87) PCT Pub. No.: WO2013/152087
PCT Pub. Date: Oct. 10, 2013

(65) Prior Publication Data
US 2015/0057515 A1    Feb. 26, 2015

Related U.S. Application Data

(60) Provisional application No. 61/620,069, filed on Apr. 4, 2012.

(51) Int. Cl.
*G01N 27/327* (2006.01)
*A61B 5/00* (2006.01)
(Continued)

(52) U.S. Cl.
CPC ....... *G01N 27/3273* (2013.01); *A61B 5/1477* (2013.01); *A61B 5/14517* (2013.01);
(Continued)

(58) Field of Classification Search
CPC .............. A61B 5/14532; A61B 5/4266; A61B 10/0064; A61B 5/14546; A61B 5/6833;
(Continued)

(56) References Cited

U.S. PATENT DOCUMENTS 3,552,929 A * 1/1971 Fields .................... A61B 5/441
                                                    422/424
4,190,060 A    2/1980 Greenleaf et al.
(Continued)

FOREIGN PATENT DOCUMENTS

CA    2869469 A1    10/2013
CN    1874720 A    12/2006
(Continued)

OTHER PUBLICATIONS

International Searching Authority, Search Report and Written Opinion issued in International Application No. PCT/US2014/061098 dated Dec. 19, 2014, 13 pages.
(Continued)

*Primary Examiner* — Christian Jang
*Assistant Examiner* — Karen E Toth
(74) *Attorney, Agent, or Firm* — Wood Herron & Evans LLP

(57) ABSTRACT

Biological chemicals, potentially found in blood are measured by collecting sweat and determining the concentration or meaning of the selected chemical in sweat. The sweat can
(Continued)

be collected using a time based, interval collector and analyzed using an external device. It can also be collected on a one time basis, using a flexible, chemical capacitor, or on a continuous basis using a chemical, field effect transducer.

15 Claims, 4 Drawing Sheets

(51) Int. Cl.
*A61B 10/00* (2006.01)
*A61B 5/145* (2006.01)
*A61B 5/1477* (2006.01)
*B01L 3/00* (2006.01)
*G01N 27/414* (2006.01)

(52) U.S. Cl.
CPC .......... *A61B 5/14546* (2013.01); *A61B 5/681* (2013.01); *A61B 10/0064* (2013.01); *B01L 3/5023* (2013.01); *G01N 27/4145* (2013.01); *A61B 5/0002* (2013.01); *A61B 5/14532* (2013.01); *A61B 10/0096* (2013.01); *B01L 2200/0621* (2013.01); *B01L 2300/022* (2013.01); *B01L 2300/023* (2013.01); *B01L 2300/069* (2013.01); *B01L 2300/0645* (2013.01); *B01L 2300/0803* (2013.01); *B01L 2300/0864* (2013.01); *B01L 2400/0406* (2013.01); *B01L 2400/0677* (2013.01); *B01L 2400/086* (2013.01)

(58) Field of Classification Search
CPC ........ A61B 2560/0412; A61B 5/14517; A61B 5/1477; A61B 10/0045; A61M 2202/092
See application file for complete search history.

(56) References Cited

U.S. PATENT DOCUMENTS

| | | | |
|---|---|---|---|
| 4,542,751 A | 9/1985 | Webster et al. | |
| 4,756,314 A * | 7/1988 | Eckenhoff | A61B 5/4266 36/182 |
| 4,820,263 A | 4/1989 | Spevak et al. | |
| 5,036,861 A | 8/1991 | Sembrowich et al. | |
| 5,050,604 A | 9/1991 | Reshef et al. | |
| 5,140,985 A * | 8/1992 | Schroeder | A61B 5/14521 600/323 |
| 5,246,003 A | 9/1993 | DeLonzor | |
| 5,438,984 A | 8/1995 | Schoendorfer | |
| 5,556,789 A | 9/1996 | Goerlach-Graw et al. | |
| 5,814,599 A | 9/1998 | Mitragotri et al. | |
| 5,944,662 A * | 8/1999 | Schoendorfer | A61B 5/14521 600/362 |
| 6,132,975 A | 10/2000 | Kanan et al. | |
| 6,198,953 B1 | 3/2001 | Webster et al. | |
| 6,256,533 B1 | 7/2001 | Yuzhakov et al. | |
| 6,269,265 B1 | 7/2001 | Anderson | |
| 6,299,578 B1 | 10/2001 | Kurnik et al. | |
| 6,479,015 B1 * | 11/2002 | Long | C12Q 1/26 422/419 |
| 6,592,529 B2 | 7/2003 | Marett | |
| 6,666,821 B2 | 12/2003 | Keimel | |
| 7,190,986 B1 | 3/2007 | Annula et al. | |
| 7,219,534 B2 | 5/2007 | Campbell | |
| 7,378,054 B2 | 5/2008 | Karmali | |
| 7,383,072 B2 | 6/2008 | Edmonson et al. | |
| 7,384,396 B2 | 6/2008 | Samuels et al. | |
| 7,749,445 B2 | 7/2010 | Masters | |
| 7,813,780 B2 | 10/2010 | Shah et al. | |
| 7,842,234 B2 | 11/2010 | Lauks et al. | |
| 7,959,791 B2 | 6/2011 | Kjaer et al. | |
| 8,125,539 B2 | 2/2012 | Takashima | |
| 8,128,889 B2 | 3/2012 | Fujimoto et al. | |
| 8,252,248 B2 | 8/2012 | Kramer | |
| 8,391,946 B2 | 3/2013 | Sugenoya et al. | |
| 8,593,287 B2 | 11/2013 | Hayter et al. | |
| 8,617,067 B2 | 12/2013 | Jain et al. | |
| 9,133,024 B2 | 9/2015 | Phan et al. | |
| 2002/0091312 A1 | 7/2002 | Berner et al. | |
| 2003/0135100 A1 | 7/2003 | Kim et al. | |
| 2003/0191376 A1 | 10/2003 | Samuels et al. | |
| 2003/0201194 A1 | 10/2003 | Heller et al. | |
| 2004/0249310 A1 | 12/2004 | Shartle et al. | |
| 2004/0267189 A1 | 12/2004 | Mavor et al. | |
| 2005/0069925 A1 | 3/2005 | Ford et al. | |
| 2005/0106713 A1 * | 5/2005 | Phan | B01L 3/50273 435/287.2 |
| 2005/0177035 A1 | 8/2005 | Botvinick et al. | |
| 2005/0192528 A1 | 9/2005 | Tapper | |
| 2005/0197554 A1 | 9/2005 | Polcha | |
| 2006/0004271 A1 | 1/2006 | Peyser et al. | |
| 2006/0062852 A1 | 3/2006 | Holmes | |
| 2006/0127964 A1 | 6/2006 | Ford et al. | |
| 2006/0253011 A1 | 11/2006 | Edmonson et al. | |
| 2006/0254341 A1 | 11/2006 | Campbell | |
| 2007/0027383 A1 | 2/2007 | Peyser et al. | |
| 2007/0032731 A1 | 2/2007 | Lovejoy et al. | |
| 2007/0179371 A1 | 8/2007 | Peyser et al. | |
| 2008/0015494 A1 | 1/2008 | Santini et al. | |
| 2008/0045816 A1 | 2/2008 | Jang et al. | |
| 2008/0154179 A1 | 6/2008 | Cantor | |
| 2008/0286349 A1 | 11/2008 | Nomoto et al. | |
| 2008/0306362 A1 * | 12/2008 | Davis | A61B 5/14521 600/307 |
| 2009/0076345 A1 * | 3/2009 | Manicka | A61B 5/0205 600/301 |
| 2009/0204008 A1 | 8/2009 | Beilin | |
| 2009/0270704 A1 | 10/2009 | Peyser et al. | |
| 2010/0044224 A1 | 2/2010 | Kataky | |
| 2010/0063372 A1 | 3/2010 | Potts et al. | |
| 2010/0130843 A1 | 5/2010 | Caceres Galvez et al. | |
| 2010/0132485 A1 | 6/2010 | Erez et al. | |
| 2010/0179403 A1 | 7/2010 | Martinsen et al. | |
| 2010/0198521 A1 * | 8/2010 | Haick | B82Y 15/00 702/19 |
| 2010/0234702 A1 * | 9/2010 | Tokita | A61B 5/14521 600/309 |
| 2011/0079521 A1 * | 4/2011 | Revol-Cavalier | A61B 5/4266 205/789 |
| 2011/0118656 A1 | 5/2011 | Eckhoff et al. | |
| 2011/0178380 A1 | 7/2011 | Chowdhury | |
| 2011/0196283 A1 | 8/2011 | Imran et al. | |
| 2011/0208458 A1 | 8/2011 | Pinter et al. | |
| 2011/0275918 A1 * | 11/2011 | Yamashita | A61B 5/14521 600/345 |
| 2012/0004570 A1 | 1/2012 | Shimizu et al. | |
| 2012/0028283 A1 | 2/2012 | Hoss et al. | |
| 2012/0123220 A1 | 5/2012 | Iyer et al. | |
| 2012/0165626 A1 | 6/2012 | Irina et al. | |
| 2012/0209226 A1 | 8/2012 | Simmons et al. | |
| 2012/0229661 A1 | 9/2012 | Sekiguchi et al. | |
| 2012/0277697 A1 | 11/2012 | Haghooie | |
| 2012/0285829 A1 | 11/2012 | Mount et al. | |
| 2012/0317430 A1 | 12/2012 | Rahman et al. | |
| 2012/0323097 A9 | 12/2012 | Chowdhury | |
| 2013/0006079 A1 | 1/2013 | Feldman et al. | |
| 2013/0010108 A1 | 1/2013 | Hashizume et al. | |
| 2013/0013028 A1 | 1/2013 | Kriksunov et al. | |
| 2013/0053668 A1 | 2/2013 | Lin | |
| 2013/0079605 A1 | 3/2013 | Bandaru et al. | |
| 2013/0099937 A1 | 4/2013 | Azimi | |
| 2013/0108667 A1 | 5/2013 | Soikum et al. | |
| 2013/0123595 A1 | 5/2013 | Currie et al. | |
| 2013/0183399 A1 | 7/2013 | Blow et al. | |
| 2013/0245388 A1 | 9/2013 | Rafferty et al. | |
| 2013/0306491 A1 | 11/2013 | Briman et al. | |
| 2013/0317333 A1 | 11/2013 | Yang et al. | |
| 2014/0012114 A1 | 1/2014 | Zevenbergen et al. | |
| 2014/0025000 A1 | 1/2014 | Currie et al. | |
| 2014/0206977 A1 | 7/2014 | Bahney et al. | |
| 2014/0275862 A1 | 9/2014 | Kennedy | |
| 2014/0276220 A1 | 9/2014 | Briscoe et al. | |

(56) References Cited

U.S. PATENT DOCUMENTS

| | | |
|---|---|---|
| 2014/0343371 A1 | 11/2014 | Sowers, II et al. |
| 2015/0057515 A1 | 2/2015 | Hagen et al. |
| 2015/0112164 A1* | 4/2015 | Heikenfeld .......... A61B 5/0537 600/307 |
| 2015/0112165 A1 | 4/2015 | Heikenfeld |
| 2016/0058354 A1 | 3/2016 | Phan et al. |
| 2016/0066828 A1 | 3/2016 | Phan et al. |
| 2016/0157768 A1 | 6/2016 | Braig et al. |

FOREIGN PATENT DOCUMENTS

| | | |
|---|---|---|
| CN | 1969184 A | 5/2007 |
| CN | 1984716 A | 6/2007 |
| CN | 101489470 A | 7/2009 |
| EP | 0282349 A2 | 9/1988 |
| EP | 0453283 A1 | 10/1991 |
| EP | 0634215 A1 | 1/1995 |
| EP | 1500937 A1 | 1/2005 |
| EP | 1637889 A1 | 3/2006 |
| EP | 2551784 A1 | 1/2013 |
| JP | H07-77525 A | 3/1995 |
| JP | H08-504513 A | 5/1996 |
| JP | 2007503958 A | 3/2007 |
| JP | 2007532260 A | 11/2007 |
| JP | 2008505330 A | 2/2008 |
| JP | 200963597 A | 3/2009 |
| JP | 2009118420 A | 5/2009 |
| WO | 9011519 A1 | 10/1990 |
| WO | 9414062 A1 | 6/1994 |
| WO | 0014535 A1 | 3/2000 |
| WO | 01/88525 A1 | 11/2001 |
| WO | 2006133101 A2 | 12/2006 |
| WO | 2007097754 A1 | 8/2007 |
| WO | 2007146047 A1 | 12/2007 |
| WO | 2008083687 A1 | 7/2008 |
| WO | 2008095940 A1 | 8/2008 |
| WO | 2009004001 A1 | 1/2009 |
| WO | 2009019686 A2 | 2/2009 |
| WO | 2009052321 A2 | 4/2009 |
| WO | 2010/017578 A1 | 2/2010 |
| WO | 2010075115 A2 | 7/2010 |
| WO | 2011117952 A1 | 9/2011 |
| WO | 2013152087 A2 | 10/2013 |
| WO | 2013181436 A1 | 12/2013 |
| WO | 2014001577 A1 | 1/2014 |
| WO | 2014025430 A2 | 2/2014 |
| WO | 2015184072 A1 | 12/2015 |
| WO | 2015184097 A2 | 12/2015 |
| WO | 2016061362 A2 | 4/2016 |
| WO | 2016/090189 A1 | 6/2016 |

OTHER PUBLICATIONS

International Searching Authority, Search Report and Written Opinion issued in International Application No. PCT/US2014/061083 dated Mar. 31, 2015, 18 pages.

International Searching Authority, Search Report and Written Opinion issued in International Application No. PCT/US2015/032830 dated Aug. 14, 2015, 9 pages.

International Searching Authority, Search Report and Written Opinion issued in International Application No. PCT/US2015/032843 dated Oct. 26, 2015, 11 pages.

International Searching Authority, Search Report and Written Opinion issued in International Application No. PCT/US2015/032866 dated Nov. 19, 2015, 12 pages.

International Searching Authority, Search Report and Written Opinion issued in International Application No. PCT/US2015/032893 dated Nov. 13, 2015, 14 pages.

International Searching Authority, Search Report and Written Opinion issued in International Application No. PCT/US2015/040113 dated Feb. 4, 2016, 13 pages.

International Searching Authority, Search Report and Written Opinion issued in International Application No. PCT/US2015/051439 dated Dec. 28, 2015, 7 pages.

International Searching Authority, Invitation to Pay Additional Search Fees and, Where Applicable, Protest Fee, and Communication Relating to the Results of the Partial International Search, issued in International Application No. PCT/US2015/032843 dated Aug. 18, 2015, 2 pages.

International Searching Authority, Invitation to Pay Additional Search Fees and, Where Applicable, Protest Fee, and Communication Relating to the Results of the Partial International Search, issued in International Application No. PCT/US2015/040113 dated Dec. 1, 2015, 2 pages.

International Searching Authority, Invitation to Pay Additional Search Fees and, Where Applicable, Protest Fee, and Communication Relating to the Results of the Partial International Search, issued in International Application No. PCT/US2015/032866 dated Aug. 31, 2015, 2 pages.

International Searching Authority, Invitation to Pay Additional Search Fees and, Where Applicable, Protest Fee, and Communication Relating to the Results of the Partial International Search, issued in International Application No. PCT/US2015/032893 dated Aug. 31, 2015, 2 pages.

International Searching Authority, Search Report and Written Opinion issued in International Application No. PCT/US16/18635 dated May 6, 2016, 12 pages.

International Searching Authority, Search Report and Written Opinion issued in International Application No. PCT/US16/17726 dated May 12, 2016, 9 pages.

International Bureau, Notification Concerning Transmittal of International Preliminary Report on Patentability issued in International Application No. PCT/US13/35092 dated Oct. 7, 2014, 14 pages.

International Searching Authority, Invitation to Pay Additional Fees and, Where Applicable, Protest Fee, and Communication Relating to the Results of the Partial International Search, issued in International Application No. PCT/US13/35092 dated Aug. 26, 2013, 9 pages.

Fu et al., "Controlled Reagent Transport in Disposable 2D Paper Networks", The Royal Society of Chemistry 2010, Lab Chip, 2010, 10, 918-920.

Chinese Patent Office, First Office Action issued in Chinese Application No. 201380028053.8 dated Dec. 21, 2015, 4 pages.

European Patent Office, Written Opinion of the International Searching Authority / International Preliminary Report on Patentability dated Oct. 16, 2014 (14 pages).

International Searching Authority, Search Report and Written Opinion issued in International Application No. PCT/US2017/039421 dated Sep. 6, 2017, 10 pages.

International Searching Authority, Search Report and Written Opinion issued in International Application No. PCT/US2017/040588 dated Sep. 25, 2017, 11 pages.

Australian Patent Office, Patent Examination Report No. 1 issued in Australian Application No. 2013243541 dated Nov. 25, 2016, 4 pages.

European Patent Office, Partial European Search Report issued in European Application No. 16203346.8-1657 dated Mar. 24, 2017, 7 pages.

International Searching Authority, Search Report and Written Opinion issued in International Application No. PCT/US16/59392 dated Oct. 28, 2016, 13 pages.

International Searching Authority, Search Report and Written Opinion issued in International Application No. PCT/US16/50928 dated Sep. 9, 2016, 8 pages.

Japanese Patent Office, Office Action issued in Japanese Application No. 2015-504702 dated Jan. 20, 2017, 7 pages (including English language translation).

Stoppa, Matteo, et. al., "Wearable Electronics and Smart Tectiles: A Critical Review," Sensors, 2014, pp. 11957-11992, vol. 14 (36 pages).

International Searching Authority, Search Report and Written Opinion issued in International Application No. PCT/US16/43862 dated Oct. 19, 2016, 14 pages.

(56) References Cited

OTHER PUBLICATIONS

Chinese Patent Office, Second Office Action issued in Chinese Application No. 201380028053.8 dated Sep. 20, 2016, 8 pages (including English language translation).
Chinese Patent Office, Third Office Action issued in Chinese Application No. 201380028053.8 dated Mar. 20, 2017, 17 pages (including English language translation).
Australian Patent Office, Notice of Acceptance for Patent Application issued in Australian Application No. 2013243541 dated Mar. 23, 2017 (3 pages).
International Searching Authority, Search Report and Written Opinion issued in corresponding International Application No. PCT/US2017/013453 dated May 18, 2017, 14 pages.
European Patent Office, Official Communication for EP Application No. 13 718 933.8-1101 dated Feb. 14, 2018 (5 pages).
European Patent Office, Extended European Search Report issued in European Application No. 15819306.0-1115 dated Feb. 9, 2018 (9 pages).
International Searching Authority, Search Report and Written Opinion issued in International Application No. PCT/US2017/067495 dated Mar. 1, 2018, 10 pages.
International Searching Authority/US, International Search Report and Written Opinion issued in corresponding PCT Application No. PCT/US2016/059392, dated Feb. 15, 2017 (12 pages).
European Patent Office, Extended Search Report issued in European Application No. 15844313.5 dated Mar. 15, 2018, 15 pages.
De Jong, J. et al., "Membranes and microfluidics: a review," Lab Chip, 2006, 6, 1125-1139 (15 pages).
Yamazaki, T. et al., "Smart Integrated Sensor for Multiple Detections of Glucose and L-Lactate Using On-Chip Electrochemical System," Journal of Sensors, vol. 2011, Article ID 190284, doi:10.1155/2011/190284, Accepted Apr. 26, 2011, 7 pages.
European Patent Office, Extended European Search Report issued for European Patent Application No. 15800043.0, dated Apr. 16, 2018, 11 pages.
European Patent Office, Supplemental European Search Report issued in European Application No. 15799514.3-1657 dated Dec. 7, 2017, 8 pages.
European Patent Office, Supplemental European Search Report issued in European Application No. 15799317.1-1657 dated Dec. 21, 2017, 9 pages.
European Patent Office, Partial European Search Report issued in European Application No. 15800043.0-115 dated Jan. 8, 2018, 13 pages.
International Searching Authority, Search Report and Written Opinion issued in International Application No. PCT/US2017/047574 dated Nov. 16, 2017, 14 pages.
International Searching Authority, Search Report and Written Opinion issued in International Application No. PCT/US2017/052651 dated Dec. 12, 2017, 14 pages.
Pike, Douglas J., et al., "Flow Cell Design for Effective Biosensing," Sensors, ISSN 1424-8220, Dec. 2012, vol. 13, pp. 58-70, www.mdpi.com/journal/sensors, 13 pages.
Sonner, Z., et al., "The microfluidics of the eccrine sweat gland, including biomarker partitioning, transport, and biosensing implications," Biomicrofluidics, vol. 9, p. 031301-1-031301-19, CrossMark, 19 pages.
European Search Report in European Patent Application No. 19173145.4, dated Jul. 30, 2019, 5 pgs.
European Search Report in European Patent Application No. 19173149.6, dated Aug. 23, 2019, 6 pgs.

\* cited by examiner

SWEAT SIMULATION, COLLECTING AND SENSING SYSTEMS

RELATED APPLICATIONS

The present application is a submission under 35 U.S.C. § 371 of International Application No. PCT/US2013/035092, filed Apr. 3, 2013, which claims priority to U.S. Ser. No. 61/620,069 filed Apr. 4, 2012, the disclosures of which are hereby incorporated herein by reference in their entirety.

STATEMENT REGARDING FEDERALLY SPONSORED RESEARCH OR DEVELOPMENT

The invention was made with government support under FA8650-09-D-5037 awarded by AFMCLO/JAZ. The government has certain rights in the invention.

BACKGROUND OF THE INVENTION

Biomarkers or chemicals carried in the blood can provide significant information which enables one to diagnose ailments, health status, toxins, performance, and other physiological attributes even in advance of any physical sign. Determining the concentration of biomarkers such as electrolytes Interleukin-1α, Interleukin-1β, Interleukin-6, Tumor Necrosis Factor α, Interleukin-8, Vasoactive Intestinal Peptide, Neuropeptide Y, Substance P, Calcitonin-Gene-Related-Peptide, Orexin-A, as well as many, many other biomarkers, provides useful insight into the health of a test patient. For example, pro-inflammatory and anti-inflammatory cytokines as well as neurotransmitters such as neuropeptide-y are associated with many applications, including cardiac stress tests, stroke diagnosis, fatigue and post-traumatic-stress-disorder. Blood tests have been developed for all of these different biomarkers, however blood testing requires that blood be drawn and subsequently analyzed. As another example, direct measurement of electrolytes such as sodium and potassium provides an assessment of hydration. This is currently clinically diagnosed with a blood draw. In addition to being invasive, many biomarkers (such as stress) can be influenced by the blood draw itself. Other test fluids have also considered for determining biomarkers in blood, for example, saliva, urine and breath have all been considered but are awkward and highly prone to contamination. Utilizing implantable sensors to analyze blood is expensive and invasive and presents significant risks.

Sweat is now recently known to carry these biomarkers. However, analyzing sweat for biomarkers raises several questions including how can it be collected, tested, and how does the information on biomarkers obtainable from sweat relate to the biomarker in the blood system.

SUMMARY OF THE INVENTION

The present invention premised on the realization that sweat can be effectively collected and analyzed on a continuous or discontinuous basis to effectively provide an indication of the concentration of biomarkers in the blood system.

More particularly in one embodiment, the present invention provides a sweat collection system which allows a plurality of sweat samples to be collected over a discrete time period to allow analysis of biomarkers versus time. Further by measuring for multiple biomarkers one or more of which being a reference biomarker, one can establish ratios of the amounts of biomarkers in a test sample to provide a reliable indication of the concentration or meaning of the non-reference biomarkers in the blood system.

Further, according to the present invention, sweat can be collected and analyzed utilizing electrochemical bio-assays such as a chemical, field effect transducer (Chem-FET), ion-selective electrode analysis, and impedance spectroscopy. This can be combined with an iontophoresis electrode and a cholinergic agent such as pilocarpine to induce sweating in a non-physically active subject, which can then be collected and analyzed using the electrochemical bio-assay.

In one particular embodiment, the electrochemical bio-assay can be worn as a patch with the data collected over a prolonged period of time and transmitted in response to an external device such as a cell phone or the like, using RFID technology or Bluetooth technology as well as many other technologies.

BRIEF DESCRIPTION OF THE DRAWINGS

The objects and advantages of the present invention we further appreciate in light of the following detailed descriptions and drawings in which.

DETAILED DESCRIPTION OF THE INVENTION

Figure 1:
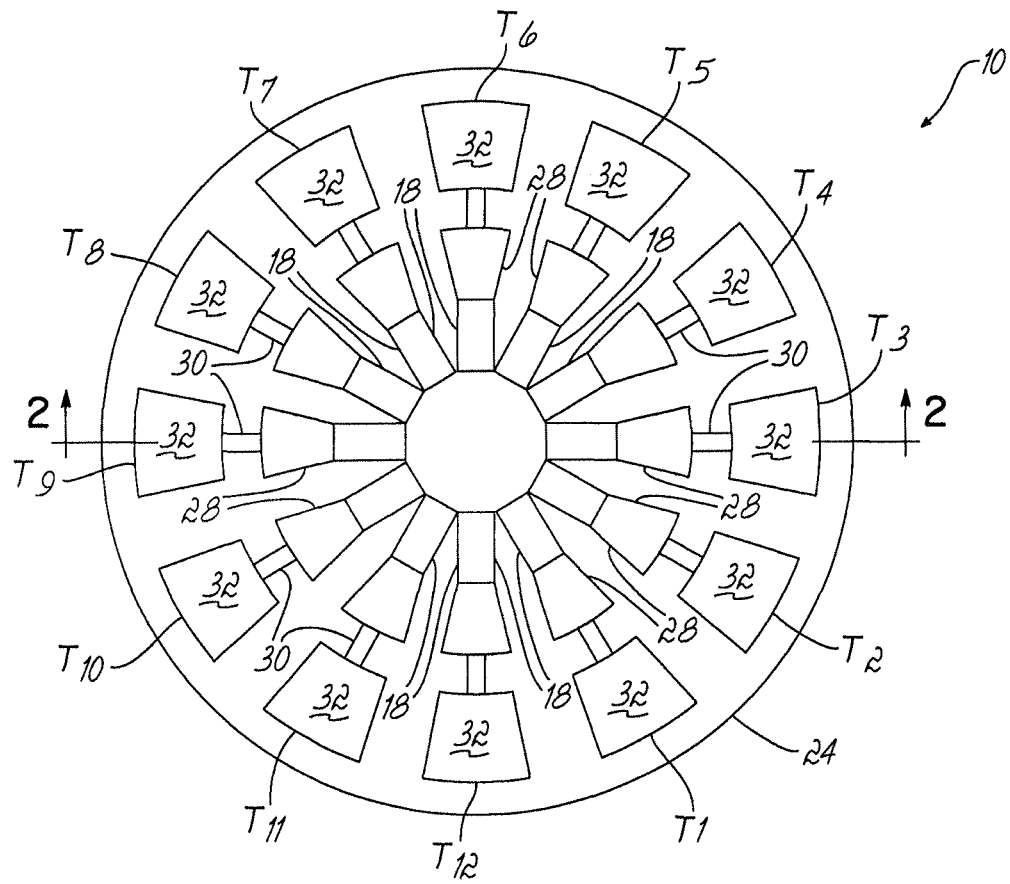
FIG. 1 is a top plan view of a time based, sweat collection system, according to the present invention.
Figure 2:
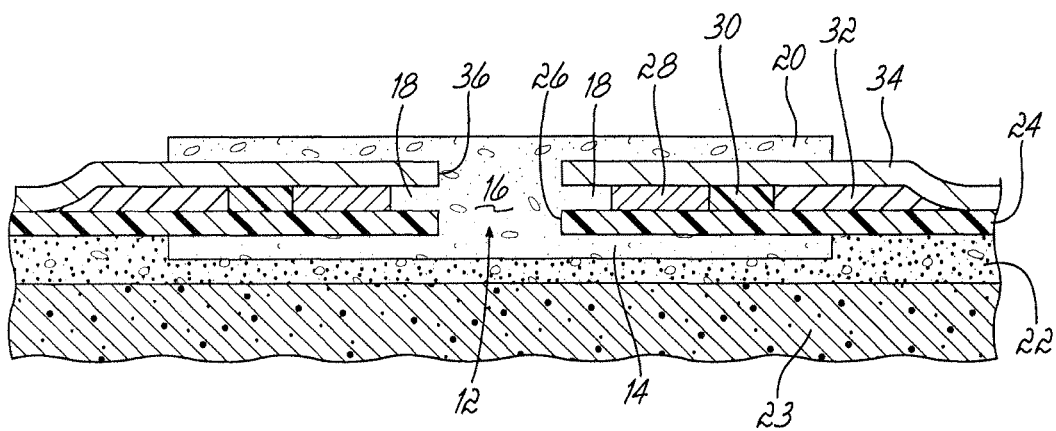
FIG. 2 is a cross-sectional view partially broken away of the sweat collection system of FIG. 1.

According to the present invention sweat is used to determine concentrations or meaning of biomarkers in blood in a non-invasive manner. As shown in FIG. 1, a sweat collector 10 that permits chronological sweat storage of a plurality of samples includes a central sweat collection member 12 having a sweat collecting central base 14 leading to a central fluid transporting core 16 leading to a plurality of arms 18. Core 16 further leads to a top portion 20 (only shown in FIG. 2) which allows for evaporation or storage of the sweat which therefore provides for continued fluid flow.

The sweat collector member 12 can be formed from any material which will readily transport sweat. Generally, a fibrous web, such as a cellulosic web, is particularly suitable for use in this application. It can be treated with a hydrophilic substance which will promote fluid flow. However, any material which will readily allow aqueous fluid flow can be used as the sweat collection member.

Sweat collection member 12 rests on a sweat porous adhesive layer 22 which permits the collector 10 to be adhered to an individual's skin 23. Separating the base 12 from the arms 18 is a water impervious flexible film 24 which has a central opening 26 corresponding with the central core 16 of the sweat collection member 12.

The radially extended arms 18 rest on the upper surface of the plastic film 24. Each arm leads to a gate member 28 which in turn extends radially outward to a bridge member 30 and finally to a collection pad 32. The arms 18, gates 28, bridges 30, and collection pads 32 are all covered with a vapor porous membrane 34 (not shown in FIG. 1, shown in FIG. 2) which also has a central opening 36 that allows the core 16 to extend through, leading to an upper fluid transporting disk 20 which simply allows fluid evaporation and flow which promotes the continued migration of sweat from the skin through the collection member 12. Disk 20 can further be coated with a super absorbent hydro gel (not shown) to further facilitate fluid flow. Alternately the disk 20 may be covered with a vapor porous membrane like that of vapor porous membrane 34. Various components of the sweat collector 10 can be arranged in multiple ways, some even excluded, so long as they satisfy the operating principles of the present invention. Furthermore, this type of sweat collector 10, may also prove useful for simple chronological collection and storage of other fluids, ranging from saliva to non-biological fluids such as river water in environmental sampling applications.

As shown in FIG. 3, the gates 28 act to delay fluid flow to the collection member 32. Each gate is slightly different from all other gates as explained below. Each of the different gates, delay the fluid flow for a different period of time so that the sweat reaches each of the collection pads at different times, thereby providing discrete chronological sweat samples at times $T_1$-$T_{12}$ as shown, with the shown 12 times being exemplary only and non-limiting. The gate 28 can be formed from a variety of different materials. One particular material suited for this application is a water soluble polymeric film member which inhibits fluid flow but gradually dissolves in the presence of a fluid like sweat. Once it dissolves, it permits sweat to flow past the gate to fill the bridge 30 and the pad 32. The different gates 28 can be formed from different thicknesses of the water soluble film or the polymeric composition of the film can be adjusted in each of the gates to establish different dissolution rates. This can be done for example by choosing film with different molecular weights. One preferred material is polyethylene oxide. The water solubility of these films can be adjusted by changing the molecular weight of the polyethylene oxide with the lower molecular weight films being more soluble. Alternately, the thickness of the film can be adjusted, with a thinner film being dissolved more quickly than a thicker film. Once the gate 28 dissolves, the sweat will pass over the gate. The gate 28 may fully dissolve, or it may simply become sweat permeable, achieved for instance with a cloth or cellulose fiber film that has been embedded with polyethylene oxide polymer.

The gates 28 are in turn in fluid communication with what are referred to as bridges 30. The bridges 30 are simply fluid conduits that only allow fluid flow for a limited period of time before they become suitably impervious to fluid flow or solute diffusion. These fluid conduits 30 will allow sweat from the gates to flow to the collection pads 32. However after a certain volume of sweat has passed through the bridge 30, it will dissolve or become impermeable to further fluid flow or solute transport, interrupting the fluid path, and preventing further sweat solutes (ions, molecules, biomarkers) from being transported into or out of the collection pad 32. Thus each collection pad 32 would receive sweat sample at a time permitted by the gate 28. When the bridge 30 dissolves, it isolates the sample on pad 32 such that the biomarker information is not blended, diluted, or distorted by sweat from later collection time periods. The present invention includes all methods that achieve this same basic functionality of sampling and isolating sweat samples, storing them in a manner that properly preserves them, and sampling and storing them in a manner which the sweat sample is representative of the sweat excreted at or near the time of sampling. The sweat collector 10 can therefore utilize alternate materials that physically or chemically change in any manner that provides similar results, including but not limited to bridges made of polymers that crosslink after some time of sweat exposure to prevent fluid flow and/or gates based on a material that slowly swells and moves into fluid connection with the next fluidic component of a sweat collector.

The bridge can be any water soluble member that has an acceptable dissolution rate. In particular, the bridge can be a polyethylene oxide thread having a fibrous surface which allows capillary migration of the sweat across a polyethylene thread. Once the thread dissolves, fluid will no longer pass to the collection pad 32 as there will be a void on the upper surface of the plastic film 24 thereby preventing further fluid flow.

The pads 32 can be tested for a variety of different biomarkers. In particular it may be desirable to analyze one or more reference biomarkers to determine the amount of a reference biomarker and compare this to a non-referenced tested biomarker, where the concentration of the referenced biomarker is generally known. This permits one to use the ratio of the referenced biomarker to the tested biomarker to determine the concentration of the tested biomarker without knowing the volume of sweat being tested. Typical reference biomarkers include known methods such as those used to determine electrolyte balance. Some biomarkers found in sweat may degrade quickly due to enzymatic or other forms of decomposition or breakdown, and storage, preservation, chemical reacting, or other chemicals, materials, or components, may be included in or with the pad 32 to preserve the desired information provided by the biomarkers.

In use, the time specific sweat collector 10 is applied to an individual skin by placing the collector on the skin with the sweat porous adhesive 22 contacting the skin. Generally, the adhesive layer will have a protective release layer (not shown) which is removed prior to use. The individual then can continue with daily activity, or sports activity, or the like. Pilocarpine can be applied at the area where the collector is applied to induce sweat formation before or after the sweat collector 10 is applied, or sweat can be generated through natural occurring methods or other forms of stimulation. Components of multiple sweat collectors 10 may be stacked and connected with additional bridges or gates to increase the duration of use and total sample collections of the sweat collector 10.

Figure 3A:
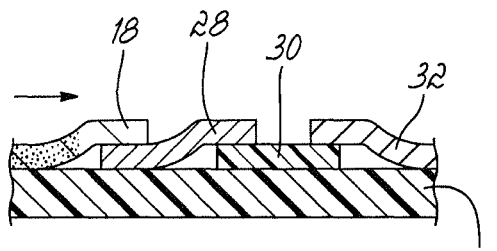
FIGS. 3A-3E are cross-sectional views of a portion of an arm of a collection system as shown in FIG. 1 showing sweat progressing through the collection arm to the collection pad over a period of time, with the sweat shown as stippled shading.
Figure 3B:
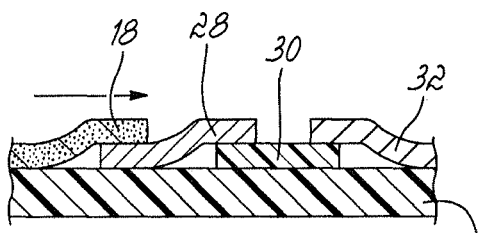
Figure 3C:
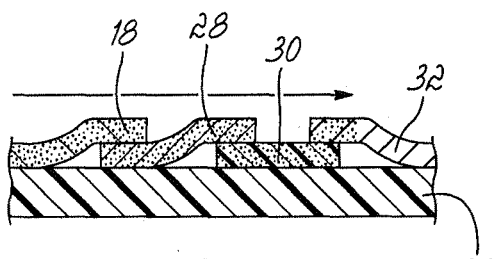
Figure 3D:
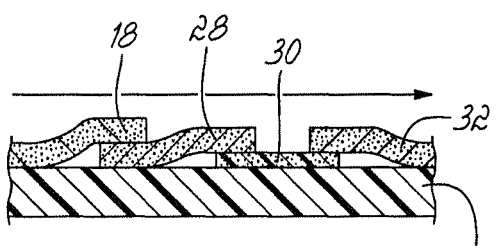
Figure 3E:
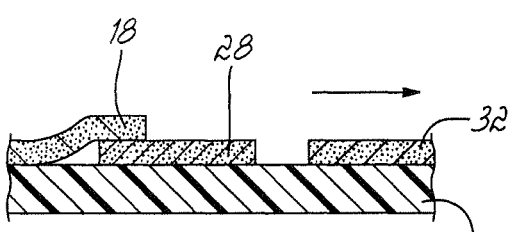

Sweat, shown as stippling in FIGS. 3A-3E, will then, as generated, travel up the central core 16 extending to the plurality of arms 18 (see FIG. 3A) and then to the individual gates 28 (see FIG. 3B). A first gate will dissolve at time T1 and a second gate at time T2 and third gate at time T3 and so on. As the gates dissolve (see FIG. 3C), sweat can migrate over the surface of dissolved polyethylene oxide film. The polyethylene oxide fiber bridge 30 will allow sweat to immediately migrate to the respective collection pad 32 (See FIG. 3D). After a period of time, the bridge 30 will dissolve (See FIG. 3E), because the bridge is narrow and breaks up by capillary-breakup, there is none or not enough polymer to allow sweat to continue to the pad 32. Thus, a first pad will stop collecting sweat at time T1+X, and a second pad at T2+X, and a third pad at T3+X, and so on, with X being the time required for the bridge 30 to dissolve. The time X could also be a variable controlled, especially so if time-averaged sampling is desired. After a period of time, the collector 10 is removed and the individual pads are analyzed for certain biomolecules using standard analysis and apparatus such as mass spectroscopy, colorimetric spectroscopy, electrophoresis, or other biomarker measurement methods known by those skilled in the art. This will provide time-based information which allows one to correlate concentration of the biological molecules in the blood stream over a period of time, with either physical factors, such as periods of stress, or in relationship to the effects of drugs and the like.

Figure 4:
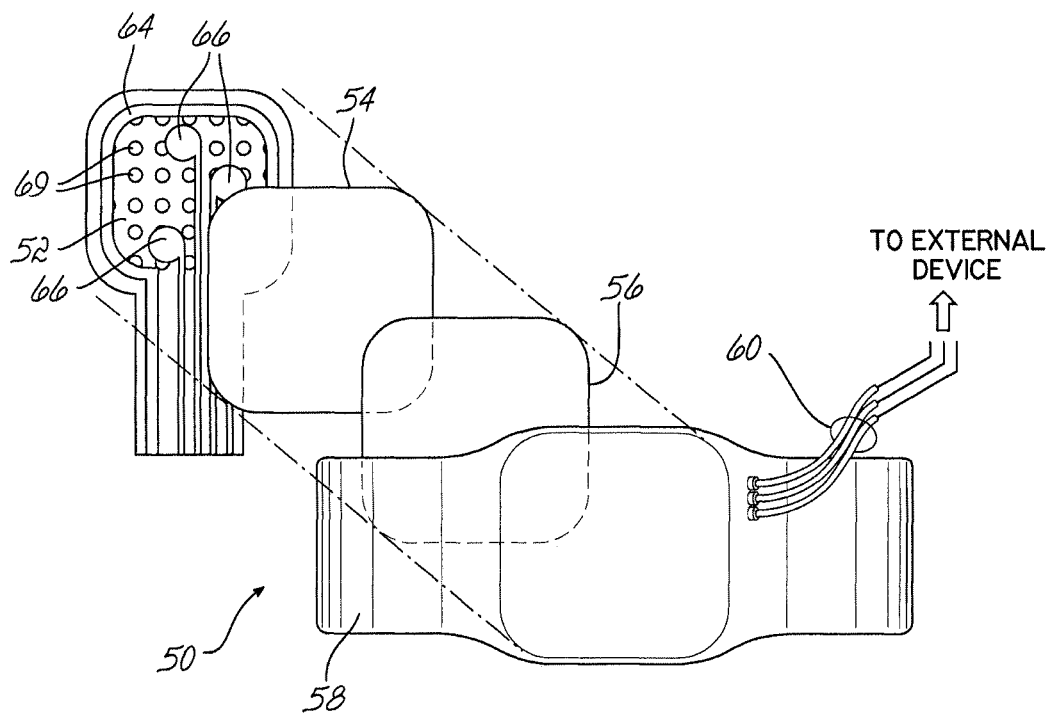
FIG. 4 is an exploded view of an alternate embodiment of the present invention.
Figure 5:
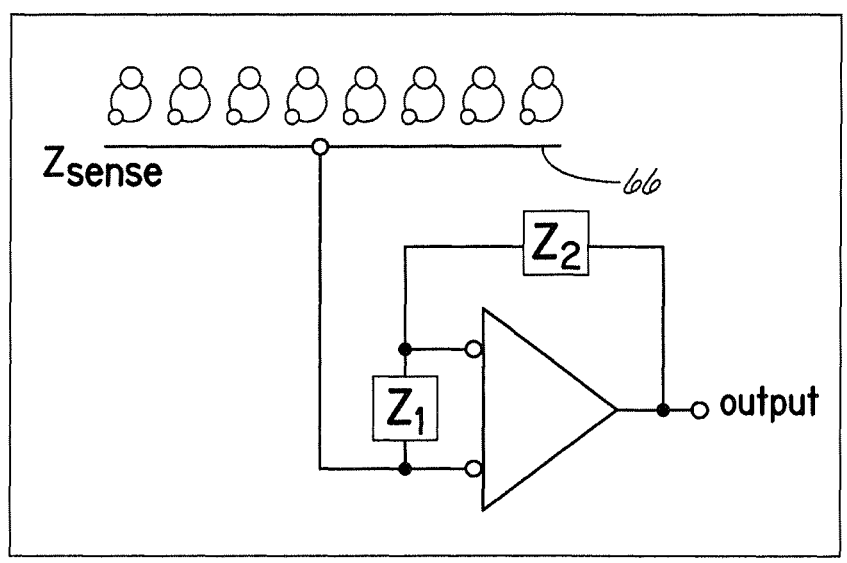
FIG. 5 is a circuit diagram of the device shown in FIG. 4.
Figure 6:
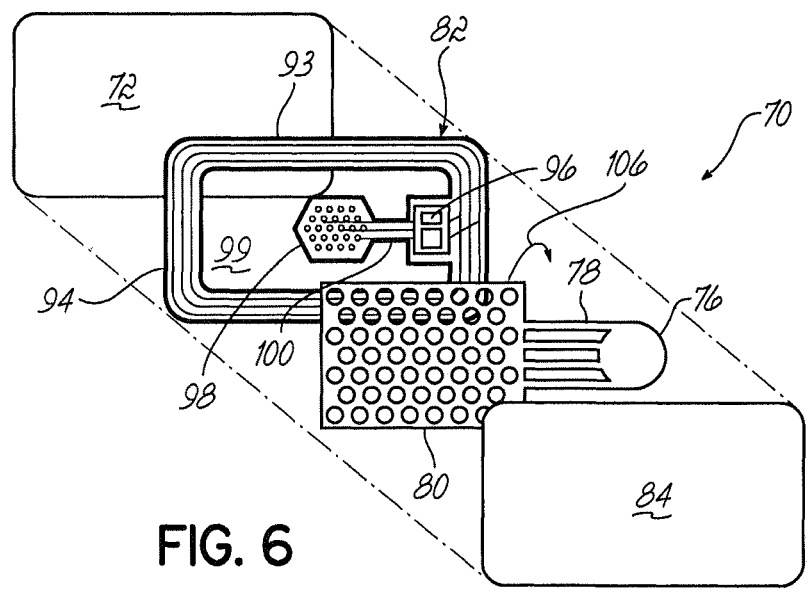
FIG. 6 is an exploded view of a second alternate embodiment of the present invention.
Figure 7:
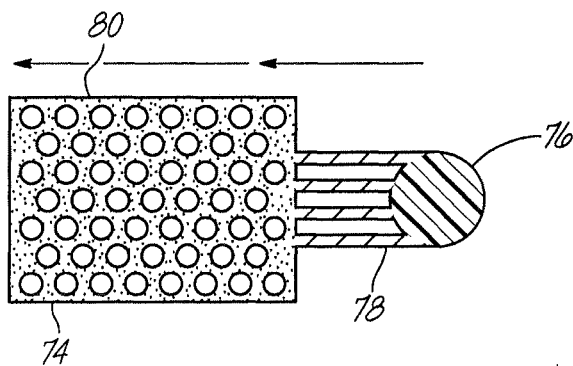
FIG. 7 is a diagrammatic top plan view of the sweat collector used in the device shown in FIG. 6.
Figure 8:
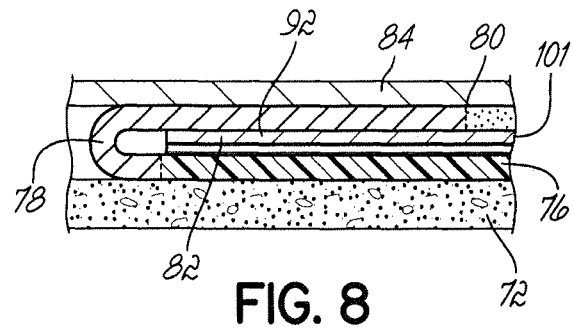
FIG. 8 is a diagrammatic cross-sectional view partially broken away of the assembled device shown in FIG. 6.
Figure 9:
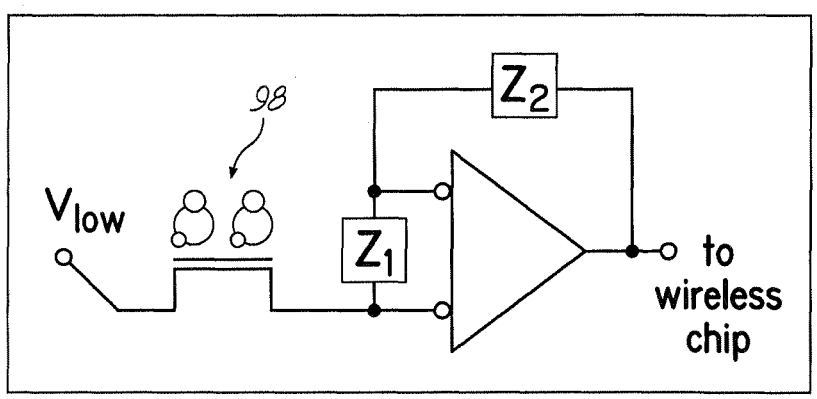
FIG. 9 is a circuit diagram of the device shown in FIG. 6.

As shown in FIGS. 4 and 5, an alternative embodiment of the present invention, is a one-time use sweat collector/sensor 50 referred simply to as the disposable sensor 50. This apparatus is designed to quickly generate and absorb sweat in a short period of time and allow immediate electrical detection of biomarkers. The disposable sensor 50 is either fully disposable or just portions thereof are disposable, with the primary feature being fast stimulation and sensing of sweat in a single wearable format. The disposable sensor 50 includes a chemical capacitor 66 or other biological chemical sensor and a disk 54 which acts as a reservoir of a cholinergic agent such as pilocarpine followed by an iontophoresis electrode 56, all secured to a wristband 58. As can be seen, wiring 60 leads from the wrist band to a second apparatus which controls the disposable sensor 50. The apparatus (not shown) can be, for example, a computer, a smart phone, or simply a dedicated device designed to operate and analyze the data set forth from the chem capacitor 66.

Chem capacitor 66 is found on a planar support layer 52 and is partially functionalized with one or more molecules adapted to bind to one or more biomarkers being studied. As such, the capacitor 66 can be a very simple, planar capacitor or interdigitated electrodes, depending upon the number of biomarkers being detected. Support layer 52 includes a series of holes 69 permitting the pilocarpine to move through the layer 52 and sweat to flow in the opposite direction to the capacitors 66. Reference, ground, and working electrodes may also be included or excluded. Other suitable sensors include chemical field effect transistors, chemical electrical impedance spectroscopes and electrochemical potentiostats.

A general wiring diagram for the device 50 is shown in FIG. 5. In a preferred embodiment only the chem capacitor 66, disk 54, and electrode 56, are actually on the disposable portion of the sensor with the remaining circuitry are in the separate control apparatus or external device (not shown).

In use, the disposable sensor 50 would be strapped on an individual's wrist with the wristband 58. Other means to attach the sensor to a body part can also be employed such as adhesives, tape and the like. The location of the sensor is not particularly critical, and can be used at almost any portion of the body with adequate surface area and access to sweat pores.

Once attached, the wires 60 are attached to the control apparatus and the iontophoresis electrode 56 is activated, causing the pilocarpine to migrate from disk 54 through holes 69. This will cause the formation of sweat. Since the chem capacitor 66 is adjacent skin, it will immediately contact the sweat. If the biomarker is present in the sweat, this will immediately be detected by change in electrical charge or electrical impedance. Generally multiple biomarkers or chemicals will be detected. In particular, one may be the reference biomarker. The concentration or meaning of the remaining biomarkers can be estimated based on the concentration or meaning of the reference biomarker. Once used for a set period of time, the sensor is thrown away. Basically, any biological chemical present in blood can be detected. Primarily biomarkers which are indicative of physical state are of interest. These include but are not limited to electrolytes, glucose, lactate, pro-inflammatory cytokines, anti-inflammatory cytokines, catecholamines, neuropeptides, as well as any protein which may be present in blood.

A third embodiment of the present invention is shown in FIGS. 6-9. Continuous sensor 70 incorporates a sweat porous adhesive layer 72, and a sweat transportation medium 74. The sweat transportation medium includes a collection pad 76 resting on the adhesive layer 72, a transfer section 78, which leads to an evaporation or storage pad 80. Although shaded differently, the collection pad 76, the transfer section 78 and the evaporation pad 80 will normally be made from the same material. The transfer section 78 extends from the collection pad 76 and around a chem-field effect transducer 82. The sensor 70 includes an upper vapor porous covering 84, which allows sweat to evaporate, and thus continue to flow through the collection pad. The covering 84 may include a layer of a hydrogel (not shown) to store sweat and therefore be less reliant on evaporation of sweat.

The sweat transport medium 74 is designed to continually promote sweat transfer in only one direction through the collection pad 76, otherwise the collection pad would fill up and not provide a continuous analysis of newly-produced sweat. Therefore, the transfer section 78 is formed from a plurality of narrow strips, which reduces the fluid flow path from the collection pad 76 to the evaporation pad 80. The enlarged evaporation pad 80 promotes fluid flow both by its size and by evaporation. Thus the reduced flow permitted through the transfer section 78 and the fluid flow promotion caused by evaporation in the evaporation pad 80 provides a continuous flow of sweat through the collection pad 76 to the evaporation pad 80 without any reverse flow or undesirable levels of back-diffusion of solutes or biomarkers. The transport medium 74 can be any medium which will absorb and transfer aqueous fluids, This can, for example, be any woven or non-woven web, and particularly non-woven webs. Cellulosic fiber webs are particularly suitable for such uses. If solutes or biomarker buildup or concentration is excessive over time, the evaporation pad 80 may be replaced or washed with water. The evaporation pad may be any material or component that serves to remove fluid, including hydrogels that simply pull in fluid by wick and swell in size as they absorb the fluid. Therefore the evaporation pad may be more broadly considered as simply a sweat removal element.

Chem-FET 82 includes a flexible base plastic layer 92 formed from Kapton or similar suitable materials. Along a periphery 93 of the base layer 92 is an RFID antenna 94 and a control chip 96. In turn, the Chem-FET 82 includes a sensor section 98 which is connected to the chip 96 through a connection strip 100. As shown, the area 99 between the sensor section 98 and the RFID antenna 94 is open which allows pilocarpine to be located in the evaporation pad 80 or an adjacent layer (not shown) to promote sweat. An iontophoresis electrode can also be included adjacent the pilocarpine. When assembled, the sensor section 98 rests directly on the transfer section 78 analyzing sweat as it is transported from the skin. As shown by arrow 106, transport section and evaporation section 80 are on the side of sensor section 98 adjacent layer 84 and collection pad 76 is on the opposite side adjacent adhesive 72.

Preferably, the sensor section 98 is a gate-exposed SiC-MOS chips having three or more identical chem-FETs per biomarker. Sub-microns SiCMOS allow for MHz impedance spectroscopy. Multi-step patterning/washing may be used to immobilize biorecognition elements. Sensors are separated spatially into subgroups of identical sensors, or large sensor arrays can be formed using techniques such as photo-initiated chemical patterning. The sensors allow for continuous monitoring of multiple physiological conditions realizing larger arrays of biomarker-specific sensors. The larger arrays can determine physiological condition through semi-specific but distinct sensors by statistical determination, eliminating the need to quantify individual biomarker levels.

In another embodiment, the sensor section 98 is an electrode, or array of electrodes, which is coated with an ion-selective material. This ion-selective material allows only one type of ion to pass through to the electrode surface, thus allowing for quantitative analysis of a single molecule type, such as sodium or potassium to name two. These ion-selective sensor arrays can determine hydration status of an individual.

It is desirable to have the chip 96, which is somewhat thicker than the printed circuitry 101, face away from the skin, but it is also desirable to form everything on one surface. The chem-FET 82 is formed by electro-deposition of the circuitry on one surface of base layer 92. The central portion 99 is then cut out. Although it is preferred to have the circuiting 101 positioned on transfer section 78, due to the flexible nature of the base layer substrate 92, the sensor section 98 can be rotated 180 degrees with the circuitry 101 positioned directly against the collection pad 76, if desired.

The chip 96 can be purchased. A variety of such chips are available on the market. One particular chip which can be used for the present invention is MLX 90129 (sold by Melexis), which is capable of up to 500 micro ampsin run mode. This chip has an internal temperature sensor. Chip 96 can also control the iontophoresis electrode if present.

In operation, this device would be attached to the skin with the adhesive layer 72. A reader, such as a smart phone, would then be strapped in close proximity to the sensor 70 on a periodic basis, for example, every few minutes, the smart phone detects and records concentrations of the selected biomolecules such as neuropeptides, cytokines, electrolyte balance, and body temperature.

The continuous sensor 70 can be modified in a wide variety of ways to provide added benefits. For example, a more robust wireless protocol such as Bluetooth can be utilized, or alternate communication or power strategies can be used. For example, the sensor can include a thin layer battery and provide its own power source, and thus not rely on RFID. Both RFID and Bluetooth can be used in conjunction where RFID can be used to charge the battery when provided the proper near field communications. In addition, an upper layer of hydrogel can be incorporated to promote a greater sweat flow. Other biomarker sensing methods and sweat transport methods may be included, so long as they provide the same capability of continuous or semi-continuous monitoring of biomarkers in sweat.

The sweat collectors of the present invention can provide a wide variety of different benefits. Time-based sweat collector 10 can be used for example in a cardiac stress test, allowing cardiac cytokine biomarker mapping versus time with no blood catheter required. Iontophoretically dosing pilocarpine for less than five minutes can stimulate sweating for the duration of such a test. Sweat collector 10 can then be positioned and later analyzed using proven techniques such as mass spectrometry. The sensor 10 can be used as a non-invasive study of the chronological systemic response of a new drug treatment. It can also be used by athletes during regular athletic activity for improved sport exertion or impact studies.

The disposable sensor 50 can be used to quickly test for very specific critical biomarkers. For example, paramedics could use this device with potential stroke victims, by strapping it onto a patient's arm; there would be no need to find a vein. The device would provide sweat in 2 to 3 minutes, and detect biomarkers 1 to 2 minutes later. Three major cytokines, namely tumor necrosis factor, interleukin 1 and interleukin 6, are produced by cultured brain cells after various stimuli, such as ischemia. This provides a diagnostic test which will expedite the appropriate treatment. By selecting the appropriate biomarkers, one can even differentiate ischemic versus hemorrhagic strokes. This very specific, inexpensive sensor can also be used in a wide variety of different time critical tests.

The continuous monitor, in addition to be useful for time-based testing of athletes and in clinical studies, can also be used as a preventive control of the onset of severe depression by detecting certain cytokines and neuropeptides. It can also be used to anticipate migraine headaches, and can be used for continuous diabetes monitoring.

Both the disposable sensor as well as the continuous monitor can be used for determining hydration status rapidly and/or continuously.

This has been a description of the present invention along with a preferred method of practicing the present invention, however the invention itself should only be defined by the appended claims.

What is claimed is:

1. A device configured to be placed on a skin surface of a wearer, comprising:
   a sweat transportation medium having a collection pad and a transfer clement section;
   a sweat removal element;
   a base layer, comprising a sensor configured to take a plurality of measurements of a solute in a sweat sample;
   a vapor porous covering configured to allow an amount of sweat to evaporate therethrough from the sweat removal element; and
   a water porous adhesive layer adjacent to the collection pad and configured to be attached to the skin surface;
   wherein the collection pad is configured to absorb the sweat sample from the skin surface, wherein the transfer section has a reduced fluid flow path relative to the collection pad and the sweat removal element, and the sweat removal element is configured to remove the amount of sweat from the sweat transportation medium by evaporation, and wherein the sweat transportation medium is configured to promote a continuous sweat flow in a direction from the collection pad, through the transfer section, and into the sweat removal element, and the sweat removal element is configured to promote continuous sweat flow out of the device.

2. The device of claim 1 wherein said transfer section comprises a plurality of narrow strips, extending from said collection pad to said sweat removal element.

3. The device of claim 1, wherein the collection pad rests on the water porous adhesive layer.

4. The device of claim 3 wherein, when the device is positioned on skin, the water porous adhesive layer is adjacent the skin and the collection pad is adjacent the water porous adhesive layer.

5. The device of claim 1 further comprising a control chip and a transmitter adapted to transmit data from the device.

6. The device of claim 5, further comprising a receiver, adapted to receive a signal from an external device which activates the transmitter.

7. The device of claim 1, wherein said sensor is connected to an RFID circuit.

8. The device of claim 7 wherein said sensor is part of a chemical field effect transducer.

9. The device of claim 1 further comprising an agent for inducing sweat generation and an iontophoresis electrode.

10. The device of claim 1 wherein said sensor comprises one or more ion-selective electrodes configured to measure concentrations of one or more electrolytes.

11. The device of claim 1 wherein said sensor comprises one or more biorecognition elements configured to measure concentrations of one or more analytes.

12. The device of claim 1 wherein said sweat removal element has a larger fluid flow path relative to said collection pad.

13. The device of claim 1 wherein the sweat transportation medium is flexible.

14. The device of claim 1 wherein the base layer is flexible.

15. The device of claim 1 wherein the transfer section comprises a fiber configured to wick an amount of sweat from the collection pad and deliver the amount of sweat to the sweat removal element.

* * * * *

UNITED STATES PATENT AND TRADEMARK OFFICE
CERTIFICATE OF CORRECTION

| | |
|---|---|
| PATENT NO. | : 11,460,430 B2 |
| APPLICATION NO. | : 14/388416 |
| DATED | : October 4, 2022 |
| INVENTOR(S) | : Joshua A. Hagen et al. |

It is certified that error appears in the above-identified patent and that said Letters Patent is hereby corrected as shown below:

On the Title Page

Column 2, page 3, sixth line from bottom, "Smart Tectiles" should read -- Smart Textiles --

In the Specification

Column 1, Line 43, "have also considered" should read -- have also been considered --

Column 1, Line 56, "invention premised" should read -- Invention is premised --

Column 3, Line 21, "collector 10 may" should read -- collector 10, may --

Column 3, Line 28, "gates, delay" should read -- gates delays --

Column 4, Lines 62-63, "(See FIG. 3D)" should read -- (see FIG. 3D) --

Column 4, Line 64, "(See FIG. 3E)" should read -- (see FIG. 3E) --

Column 5, Lines 14-16, "invention, is a one-time use sweat collector/sensor 50 referred simply to as" should read -- invention is a one-time use sweat collector/sensor 50 referred to simply as --

Column 5, Lines 48-50, "56, are actually on the disposable portion ... the remaining circuitry are in the separate" should read -- 56 are actually on the disposable portion ... the remaining circuitry in the separate --

Column 6, Line 38, "pad 80 provides" should read -- pad 80 provide --

Column 7, Lines 3-4, "section 98 is a gate exposed SiC MOS chips" should read -- section 98 is a gate exposed Sic MOS chip --

Signed and Sealed this
Seventeenth Day of January, 2023

Katherine Kelly Vidal
*Director of the United States Patent and Trademark Office*

CERTIFICATE OF CORRECTION (continued)
U.S. Pat. No. 11,460,430 B2

Column 7, Line 38, "micro ampsin" should read -- micro amps in --

In the Claims

Claim 1, Column 8, Line 41, "transfer element section" should read -- transfer section --